(12) United States Patent
Bowman et al.

(10) Patent No.: US 7,819,075 B2
(45) Date of Patent: Oct. 26, 2010

(54) INHALER DEVICE COUNTER

(75) Inventors: Nic Bowman, Cambridge (GB); Douglas Bradshaw, Royston Herts (GB); Lennart Sörby, Uppsala (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 12/555,559

(22) Filed: Sep. 8, 2009

(65) Prior Publication Data

US 2010/0065649 A1 Mar. 18, 2010

Related U.S. Application Data

(63) Continuation of application No. 11/570,747, filed as application No. PCT/SE2006/000423 on Apr. 10, 2006, now Pat. No. 7,587,988.

(30) Foreign Application Priority Data

Apr. 14, 2005 (SE) .................................. 0500857

(51) Int. Cl.
*A61M 15/00* (2006.01)
(52) U.S. Cl. ...................... 116/307; 222/36; 128/205.23
(58) Field of Classification Search ................. 116/307, 116/284, 285, 296–298, 305, 306, 319, 320; 128/200.23, 203.15, 205.23, 202.22; 222/23, 222/36, 38, 41, 44; 235/103, 122, 142, 143, 235/61 R, 77
See application file for complete search history.

(56) References Cited

U.S. PATENT DOCUMENTS

| | | | |
|---|---|---|---|
| 1,936,126 A | 11/1933 | Daly | |
| 2,174,668 A | 10/1939 | Naylor | |
| 2,582,755 A | 1/1952 | Kenny | |
| 2,636,469 A | 4/1953 | McKay | |
| 4,817,822 A | 4/1989 | Rand et al. | |
| 5,002,162 A | 3/1991 | Nemoto | |
| 5,349,945 A | 9/1994 | Wass et al. | |
| 5,482,030 A | 1/1996 | Klein | |
| 6,082,358 A | 7/2000 | Scarrott et al. | |
| 6,164,494 A | 12/2000 | Marelli | |
| 6,446,627 B1 | 9/2002 | Bowman et al. | |
| 6,752,153 B1 | 6/2004 | Eckert | |
| 7,100,530 B2 | 9/2006 | Lu | |
| 7,107,986 B2 | 9/2006 | Rand et al. | |

(Continued)

FOREIGN PATENT DOCUMENTS

EP 0254391 1/1988

(Continued)

*Primary Examiner*—Amy Cohen Johnson
(74) *Attorney, Agent, or Firm*—Finnegan, Henderson, Farabow, Garrett & Dunner, LLP

(57) ABSTRACT

Inhaler counter (20) comprising a counter housing (390), a rocker arm (200) with a pawl (210), the rocker arm being pivotally supported by the housing and arranged to perform a rocker movement in response to a linear actuation motion, a return spring (220) for resetting the rocker arm, a ratchet wheel (230) engagable with the pawl to convert the movement of the rocker arm into an incremental rotational motion of an axle arrangement (240) advancing a display means (60), the axle arrangement further comprising a back rotation prevention means (280) in the form of a spring loaded friction brake and a worm gear, the display means comprising rotatable indicator means (120) with teeth that engage the worm-gear and a stationary scale.

5 Claims, 9 Drawing Sheets

U.S. PATENT DOCUMENTS

| | | |
|---|---|---|
| 7,587,988 B2 * | 9/2009 | Bowman et al. ............ 116/307 |
| 2003/0183230 A1 | 10/2003 | Nelson et al. |
| 2003/0230304 A1 | 12/2003 | Blacker et al. |

FOREIGN PATENT DOCUMENTS

| | | |
|---|---|---|
| WO | WO 95/34874 A1 | 12/1995 |
| WO | WO 02/00281 | 1/2002 |
| WO | WO 2006/027313 | 3/2006 |
| WO | WO 2006/027333 | 3/2006 |
| WO | WO 2006/054083 | 5/2006 |
| WO | WO 2006/062450 | 6/2006 |

* cited by examiner

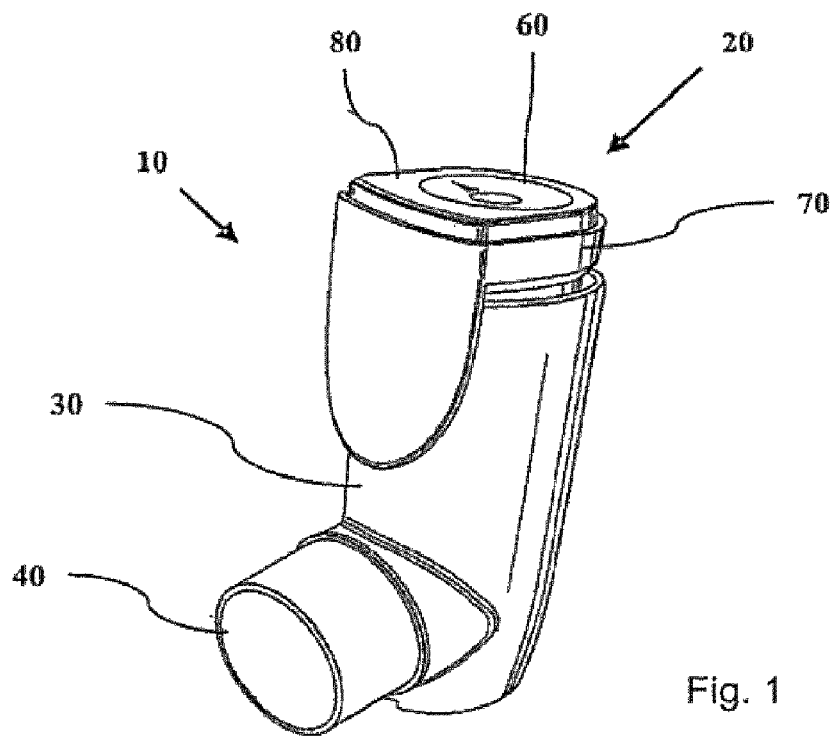
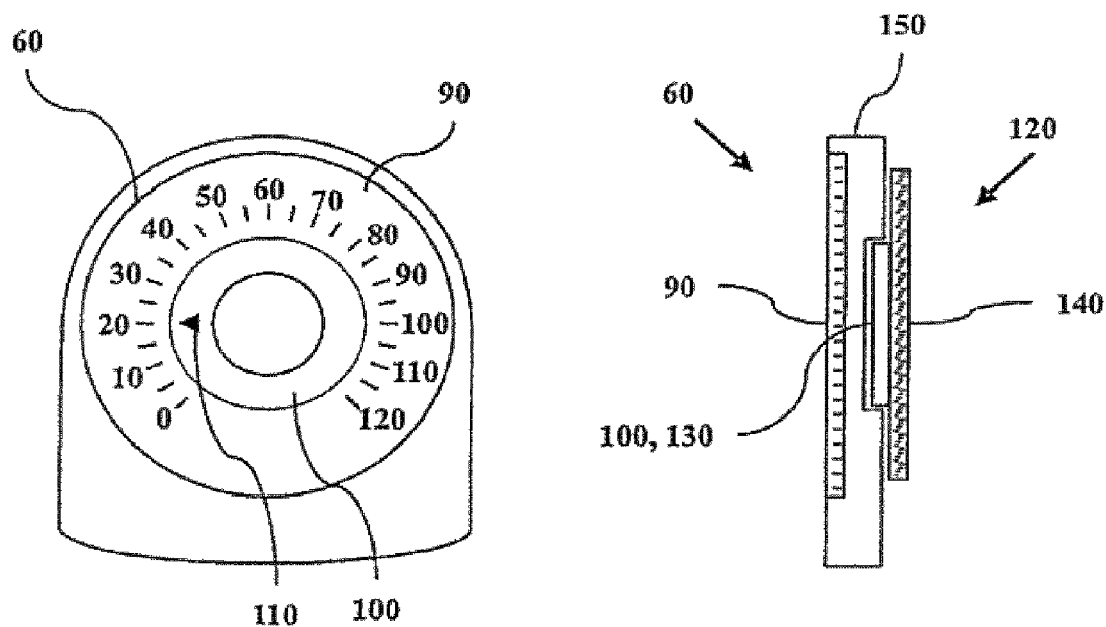
Fig. 1
Fig. 2
Fig. 3

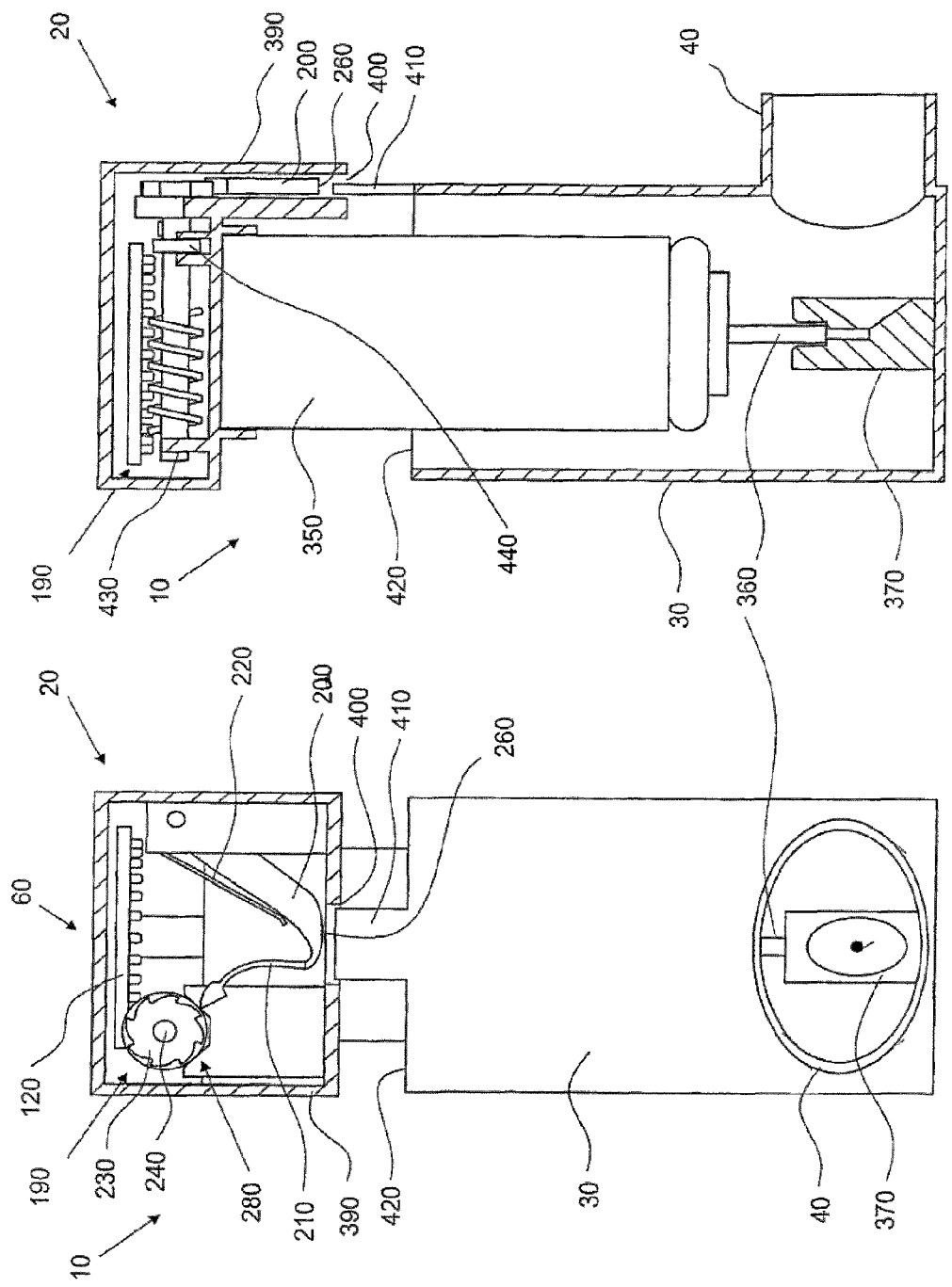

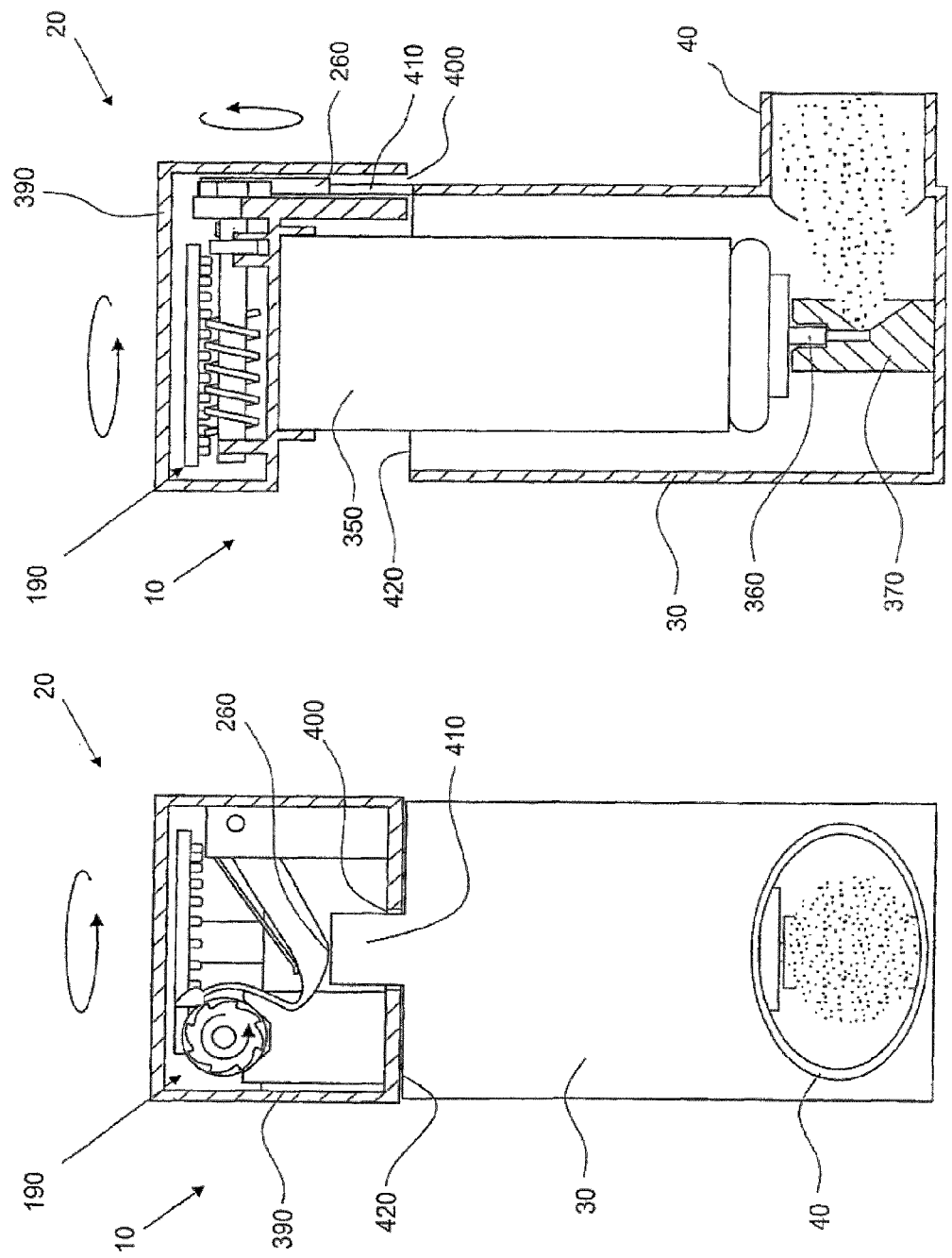

INHALER DEVICE COUNTER

CROSS-REFERENCE TO RELATED APPLICATIONS

This application is a continuation of and claims priority to U.S. application Ser. No. 11/570,747, filed Feb. 16, 2007, which is a national phase application under 35 U.S.C. §371 of PCT International Application No. PCT/SE2006/000423, filed Apr. 10, 2006, which claims priority to Swedish Application Ser. No. 0500857-8, filed Apr. 14, 2005.

The present invention relates to the art of inhaler device counters, and in particular to a counter mechanism for such.

BACKGROUND OF THE INVENTION

Many types of medicines are provided in fluid form, such as a solution or suspension of particles in a propellant or emulsion, and are adapted for oral inhalation by a patient. As one example, a container might contain asthma medicine such as fluticasone propionate.

In order to deliver medicine to the patient, the container operates in conjunction with an actuator as a system commonly known as a metered dose inhaler (MDI) system. The actuator includes a housing having an open container-loading end and an open mouthpiece. A nozzle element is disposed within the housing and includes a valve stem-receiving bore communicating with a nozzle orifice. The orifice is aimed toward the mouthpiece. In order to receive a properly metered dosage of medicine from the container, the patient installs the container into the actuator through the container-loading end until the valve stem is fitted into the receiving bore of the nozzle element. With the container so installed, the opposite end of the container typically extends to some degree outside the actuator housing. The patient then places the mouthpiece into his or her mouth and pushes downwardly on the exposed container end. This action causes the container to displace downwardly with respect to the valve stem, which in turn unseats the valve. Owing to the design of the valve, the design of the nozzle element, and between the interior of the container and the ambient air, a short burst of precisely metered, atomized medicine is thereby delivered to the patient.

Such a container is filled with a predetermined volume of active substance, i.e. medicine. Hence, the container can nominally deliver a predetermined number of medicine doses before it has to be discarded. In order to visualize the number of remaining doses in such an inhaler device, it is preferably provided with a counter that displays the amount of medicine remaining in the container. Thus, the counter gives an indication of when to replace the inhaler device or container. The display of the "present state" can either be done in absolute terms, e.g. by showing in figures the actual number of doses that are still available, or in relative terms, e.g. by a color gradient from one color to another.

Irrespective of the display type, it is of great importance that the counter mechanism does not over-count and especially not under-count. Under counting can lead to a situation where the user believes that there still are active doses in an empty inhaler, which in the worst case can be lethal. On the contrary, over counting results in that, not empty inhalers will be discharged, inhalers still containing usable doses will not be used by the patient or disposed of, whereby the user will not get full value of the product, increasing patient cost and wasted product and whereby the drug still contained in the inhaler might escape into the environment, if the discarded inhaler is not disposed of correctly. Regulatory guidelines require the over and undercounting errors to be minimised. As is discussed in detail in SE appl: 0401773-7, the count point for the counter should be positioned just before the earliest possible fire point in order to minimize the risk for under-counting. This however, leads to that the situation whereby the actuation motion will continue a distance after the count point in order to achieve actuation of the inhaler device. In fact, the metered dose valve of the inhaler device allows a relatively long continued actuation motion after the fire point. Therefore, any counter must, in addition to performing one count just before the fire point, also be able to accommodate the continued actuation motion, without double-counting etc.

In many dose counters, the relative actuation motion is transferred to an incremental rotational motion by a ratchet wheel and pawl mechanism. In order for such mechanisms to be exact and count exactly one count for each activation, the rotation of the ratchet wheel has to be controlled to exact increments. There are basically two types of means for achieving such controlled rotation:

Incrementally acting back rotation prevention means, in the form of e.g. a fixed pawl, that prevent back rotation at defined angles, and which is activated by rotation of the ratchet wheel beyond said defined angle. The ratchet wheel is thereafter rotated in the opposite direction during the reset motion of the pawl until the defined angle is reached and further rotation is stopped.

Step-less back rotation prevention means and controlled engagement and disengagement between the pawl and the ratchet wheel. Friction forces may cause a tendency of the pawl to flex radially inwardly towards the axis of rotation of the ratchet wheel at the point of disengagement, whereby the resulting angle will depend on parameters as: friction coefficient between the ratchet tooth and the pawl, the speed of the actuation motion etc. unless the disengagement is controlled.

Both systems have benefits, but the preferred option for this dose counter design is the later friction type because it reduces the effect of the assembly tolerances, therefore restricting the variation in the count point.

U.S. Pat. No. 4,817,822 describes an aerosol dispenser of the type described above having a dose indicating device which, in a first embodiment is attached to the end of the protruding portion of the aerosol container. The operating mechanism of the dose counter is of ratchet wheel and pawl (driving arm) type located within a housing that extends from the end of the aerosol container along the external surface of the tubular housing and is actuated by the relative motion between the actuator housing and the counter housing during actuation of the inhaler device. In order to accommodate for excessive actuation motion, the ratchet wheel and pawl mechanism is provided with movement restricting means that only allows the pawl to move a predetermined distance during the actuation motion, and the actuation motion is transferred to the pawl via flexible link means that allows the pawl motion to end before the actuation motion.

U.S. Pat. No. 6,446,627 discloses a dose counter for a metered dose inhaler comprises actuator means, drive means for driving a rotary gear in step-wise fashion in response to displacement of said actuator means, said rotary gear comprising a wheel having a plurality of ratchet teeth around its periphery. Means are provided to prevent reverse rotation of the rotary gear, said means preferably being step-less restraint means in the form of a friction clutch. A flexible tape is provided with a visible array of incrementing integers on its surface indicating the number of medicament doses remaining in the inhaler. The tape indexes by a single integer in response to each step of the step-wise rotary motion of the rotary gear. A separate control surface regulates the position of engagement and disengagement between the drive means and the rotary gear whereby the angle of rotation for the rotary gear is controlled for each actuation. It is specifically discussed that the control surface serves to inhibit the natural tendency of the flexible drive means to flex radially inwardly towards the axis of rotation of the ratchet-toothed wheel, and forces the drive means to disengage from the ratchet tooth at a fixed point. However, the proposed dose counter is of relatively complex design and not possible to assemble in an efficient manner.

Moreover, for hygienic reasons it is preferred that the entire inhaler is disposable, and that no parts are re-used. Therefore, the inhaler, including the counter mechanism has to be inexpensive to produce. In order for the counter to be inexpensive, it should comprise few parts and it should be simple to assemble Due to the limited size of inhalers, the counter inevitably has to be small, which especially reduces the readability of the display. This is particularly the situation for displays, showing the number of remaining doses by absolute numbers, as the figures have to be small sized in order for the counter to fit in the inhaler device.

SUMMARY OF THE INVENTION

The object of the invention is to provide a new inhaler and an inhaler counter, which inhaler and counter overcomes one or more drawbacks of the prior art. This is achieved by the inhaler and the inhaler counter as defined in the independent claims.

One advantage with such a counter is that it comprises an easy readable large display and an accurate mechanism comprised of six separate parts that are easy to assemble, whereby the counter is inexpensive to produce.

Embodiments of the invention are defined in the dependent claims.

BRIEF DESCRIPTION OF THE DRAWINGS

The invention will be described in detail below with reference to the drawings, in which FIG. 1 is a schematic perspective view of an inhaler device with a counter according to the present invention.

FIG. 2 shows a schematic display arrangement for an inhaler device counter according to the present invention.

FIG. 3 is a schematic cross sectional view of the display arrangement of FIG. 2

FIGS. 5a and 5b show the counter mechanism of FIGS. 4a to 4c, in a schematic inhaler device, partly in cross-section.

FIGS. 6a and 6b show actuation of the inhaler device and the counter of FIGS. 5a and 5b.

DETAILED DESCRIPTION OF PREFERRED EMBODIMENTS

Figure 4A:
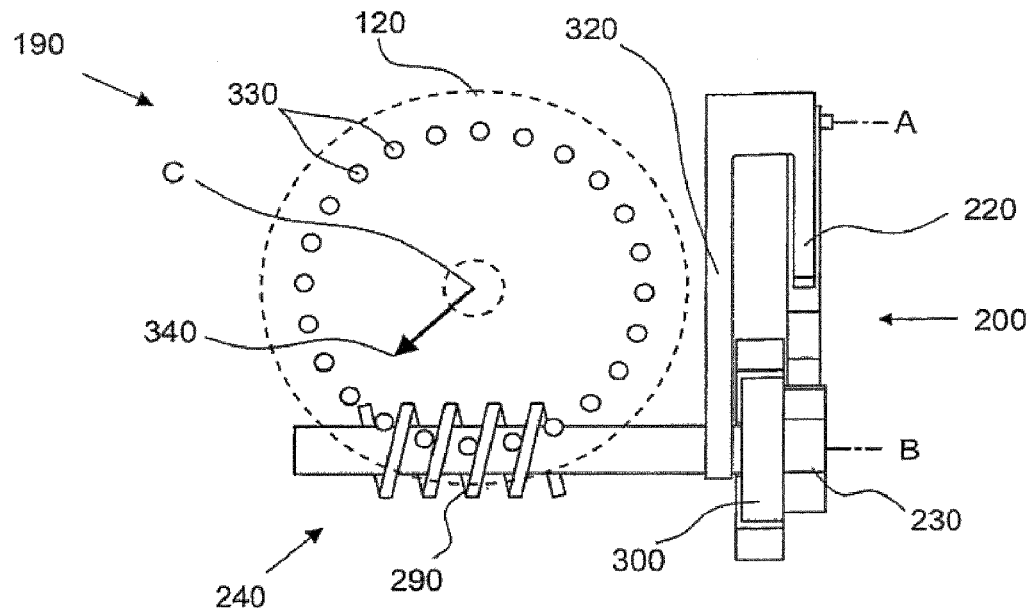
FIGS. 4a to 4c show a schematic example of a counter mechanism for an inhaler device counter according to the present invention.

FIG. 1 shows a schematic example of an inhaler device 10 comprising a counter 20 according to the present invention. The inhaler device comprises an actuator body 30 with a mouth piece 40, through which medicine is delivered to the user, and a container-counter assembly. In this embodiment the counter 20 is attached to the end of an inhaler container (not shown) arranged in the actuator housing 30. The inhaler device 10 is actuated by depressing the container-counter assembly with respect to the actuator housing 30. The counter 20 is arranged to count each actuation of the inhaler device 10, and display the actual condition, via a display arrangement 60. The counter 20 could further be arranged as a part of, or being detachably attached to the actuator housing 30, e.g. on the front or back side thereof.

According to the invention, the counter 20 is provided onto the base of the inhaler container. The counter 20 is attached to the inhaler container in an assembling process and it can be attached to the inhaler container at any one of numerous points along the canister end opposite the valve, i.e. the part of the canister opposite from the valve stem, from the outermost edge of the counter to its inside base giving ranges of variation of positions and varying lengths of canister tolerances. I.e. the counter can be attached anywhere on the base of the canister.

In this text we will refer to a fire point, which is the amount of compression of the inhaler container with respect to the actuator body that is necessary for delivering a dose of medicament and a count point, which is the amount of compression of the inhaler container with respect to the actuator body that is necessary for affecting the counter 20 to count one dose. Since undercounting is not to recommend due to the risk that the user believes that there is medicament left in the inhaler container when it actually is empty, the count point is set to be a predetermined amount less than the fire point, whereby firing without counting is effectively avoided.

The counter 20 is basically comprised of a counter housing 70, a counter mechanism (described in detail below) and a display arrangement 60. In the embodiment shown in FIG. 1 the display arrangement 60 is provided in a top surface 80 of the counter housing 70. In the disclosed embodiment, the top surface 80 of the housing 70 is provided as a transparent moulded part 150 that closes the housing 70. In the disclosed embodiment, the counter top surface 80 further is utilized as an actuating surface for actuation of the inhaler device 10, i.e. for depressing the container-counter assembly. Because the counter top surface 80 is used as actuating surface, it has to be rigid and wear resistant, as it will be subjected to compressive force and wear during the actuation of the inhaler device 10.

FIG. 2 shows a schematic top view of the counter 20 with an example of the display arrangement 60 according to the present invention. The display arrangement 60 comprises a static display section 90 and a moveable display section 100. In the disclosed embodiment, the static display section 90 surrounds the moveable section 100, which is provided as a rotatable element with a pointer 110. The static display section 90 is an annular graduation area with indices for the number of doses remaining in the container, and the angular position of the pointer 110 thus gives the actual count. With this arrangement it is possible to achieve the advantages with both relative and exact value indication of the remaining number of doses.

FIG. 3 shows the essential parts of the display arrangement 60 of the counter 20 of FIG. 2 in cross section. The moveable display section 100 is provided as a pointer wheel 120, whose rotation is controlled by the counting mechanism (described below). The pointer wheel 120 comprises a display portion 130 with the pointer 110, and a counter mechanism engaging portion 140, in the form of a toothed wheel.

Figure 4B:
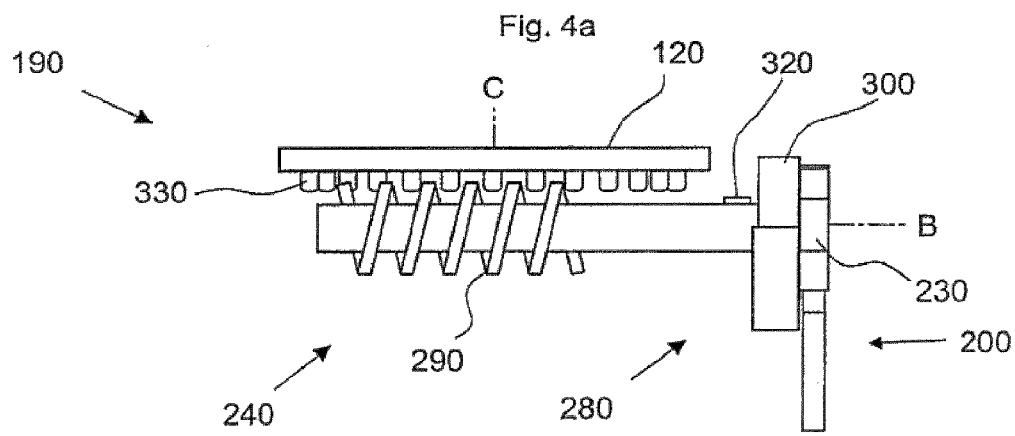
Figure 4C:
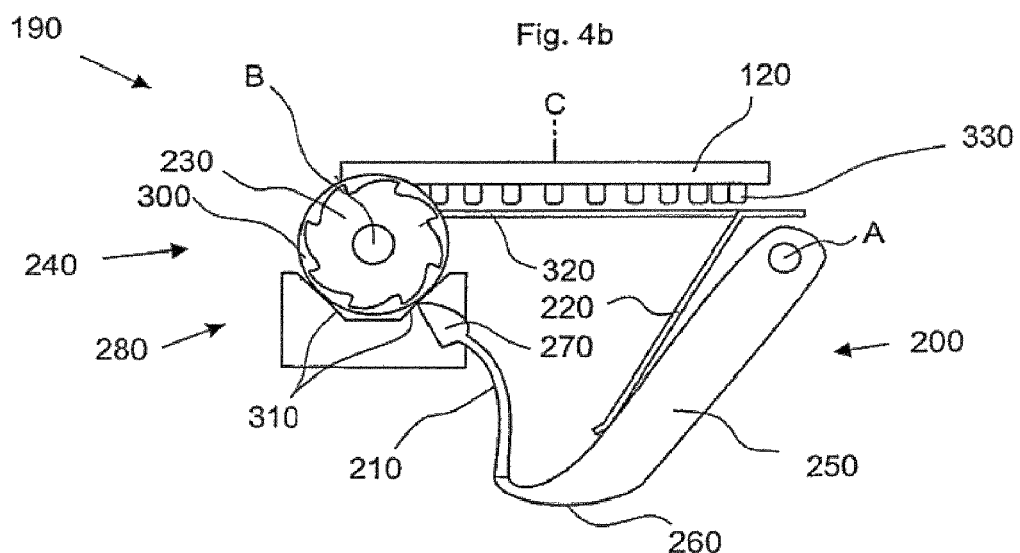

FIGS. 4a to 4c show a schematic example of a counter mechanism 190 for an inhaler device counter according to the present invention, with the housing 70 removed. The counter mechanism comprises a rocker arm 200, a return spring 220, an axle arrangement 240 with a ratchet wheel 230, and rotatable pointer wheel 120.

The rocker arm 200 comprises a pawl 210, and is pivotally supported by the housing at A, and biased in the downward direction by the return spring 220. The rocker arm 200 comprises a rigid rocker section 250 that extends from A to its lowest point 260 adjacent to the bottom of the housing where it makes contact with a protrusion from the actuator housing (as will be shown in detail later), and a flexible pawl 210 with a pawl head 270 arranged to engage and drive the ratchet wheel 230 for incremental rotational motion upon actuation motion of the inhaler.

The axle arrangement 240 comprises, in addition to the ratchet wheel 230, a back rotation prevention means 280, and a worm gear 290, all arranged on the same axle, supported by the housing (not shown) for rotation about B. The back rotation prevention means 280 is a spring loaded friction brake, comprising a brake disc 300 that is biased against two inclined friction surfaces 310 by a brake spring 320. In the present embodiment, the return spring 220 and the brake spring 320 are made as one unit with two separate "spring-beams" extending from a common fastening base for attachment to the housing (not shown). The back rotation prevention means 280 will be described more in detail later.

The pointer wheel 120 is rotatable about C, it has a peripheral rack of teeth 330 that engage the worm-gear 290 and a pointer 340 indicating the dose-count on stationary scale (not shown in FIGS. 4a-c). Thus, the pointer wheel 120 is driven for rotation about C by the worm gear 290 on the axle arrangement 240.

FIGS. 5a and 5b show the counter mechanism 190 of FIGS. 4a to 4c, in a schematic inhaler device 10, partly in cross-section. The inhaler device 10 comprises an actuator body 30, which encloses a canister 350 holding the medicament. The medicament is delivered to the user through a valve stem 360 connected at one end of the canister 350. The medicament is inhaled by the user through a mouthpiece 40 that is a part of the actuator body 30. The mouthpiece 40 is in connection with the valve stem 360 via a stem receiving body 370 for receiving the medicament to be delivered. Furthermore the dose counter unit 20 is provided at the end opposite the valve 360 of the canister 350. In the embodiments disclosed herein, the dose counter unit 20 is preferably permanently attached to the canister 350, in order to avoid that the counter unit 20 is removed from one canister 350 and attached on another canister 350 containing a different level of medicament. The canister 350 with the attached dose counter unit 20 is hereafter referred to as an inhaler can assembly. When a dose of medicament should be delivered to the user, the inhaler can assembly is pressed downwards whereby the valve stem 360 is forced into a position where it delivers a dose of medicament, or by other words is fired. This is in conformity with many inhalation devices according to the prior art and will not be described in more detail here.

The dose counter 20 comprises a counter housing 390 and a counter mechanism 190 of FIGS. 4a to 4c. The housing 80 is, in a downwards directed surface thereof, provided with an aperture 400 that is adapted to receive a protrusion 410 from the top edge 420 of the actuator body 30 in a mating relationship. When the inhaler can assembly is depressed in order to fire the inhaler device 10, as is shown in corresponding FIGS. 6a and 6b, the protrusion 410 extends through the aperture 400 into the counter housing 390 and engages the lower portion 260 of the rocker arm 200, and hence actuates the counter mechanism 190.

Figure 7:
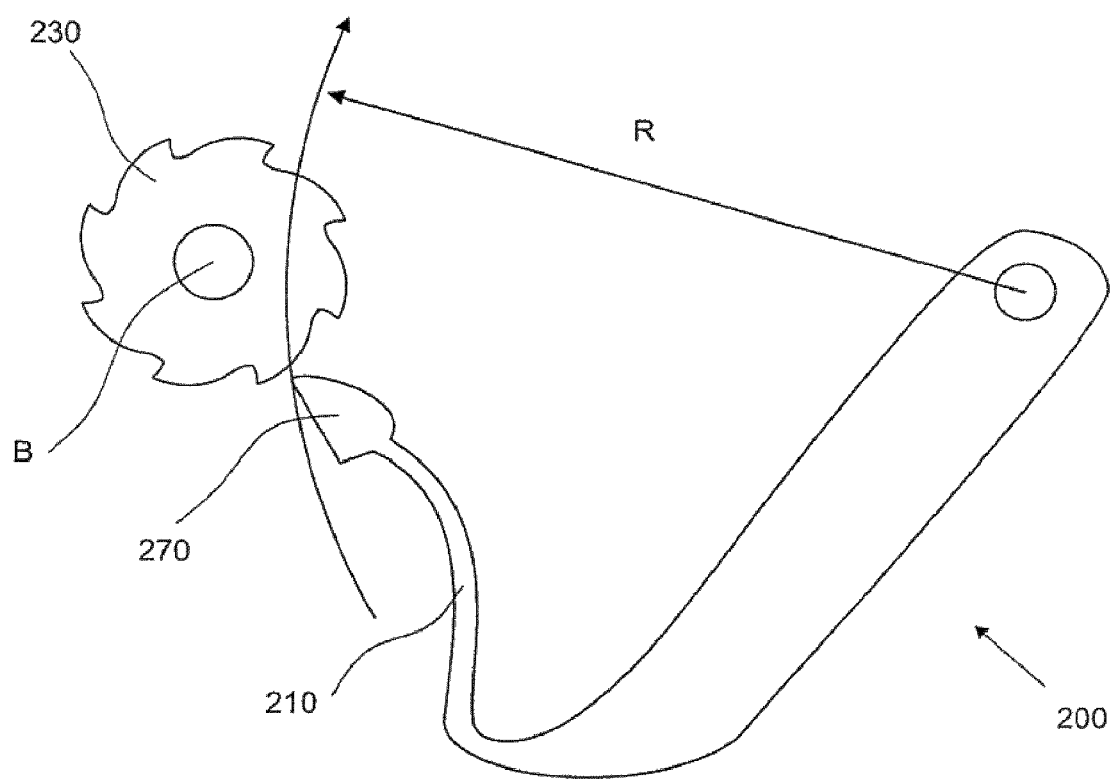
FIG. 7 shows the basic geometry of the pawl and ratchet arrangement in the counter mechanism of FIGS. 4a to 4c.

FIG. 7 shows the basic geometry of the rocker arm 200 and ratchet wheel 230 arrangement in the counter mechanism 190 of FIGS. 4a to 4c. Ideally, the pawl head 270 travels along a circle arc of radius R during the rocker motion, and the engagement with and disengagement from the ratchet wheel 230 resembles the meshing of two gear wheels. However, in order for the pawl 210 to rotate the ratchet wheel 230 a desired angle e.g. 45°, the ratchet wheel 230 is arranged closer than the ideal meshing distance whereby the motion of the pawl head 270 involves a decrease of the travel radius after engagement with the ratchet wheel 230. In this way the pawl head 270 engage the ratchet wheel 230 some angle earlier than for the ideal meshing distance and vice versa disengage some angle later. In order for the mechanism to be resetable, the rocker arm is biased in the "non-driving" direction, and the pawl 210 is flexible in the radial direction. The pawl 210 is essentially stiff in the circumferential direction.

Figure 8A:
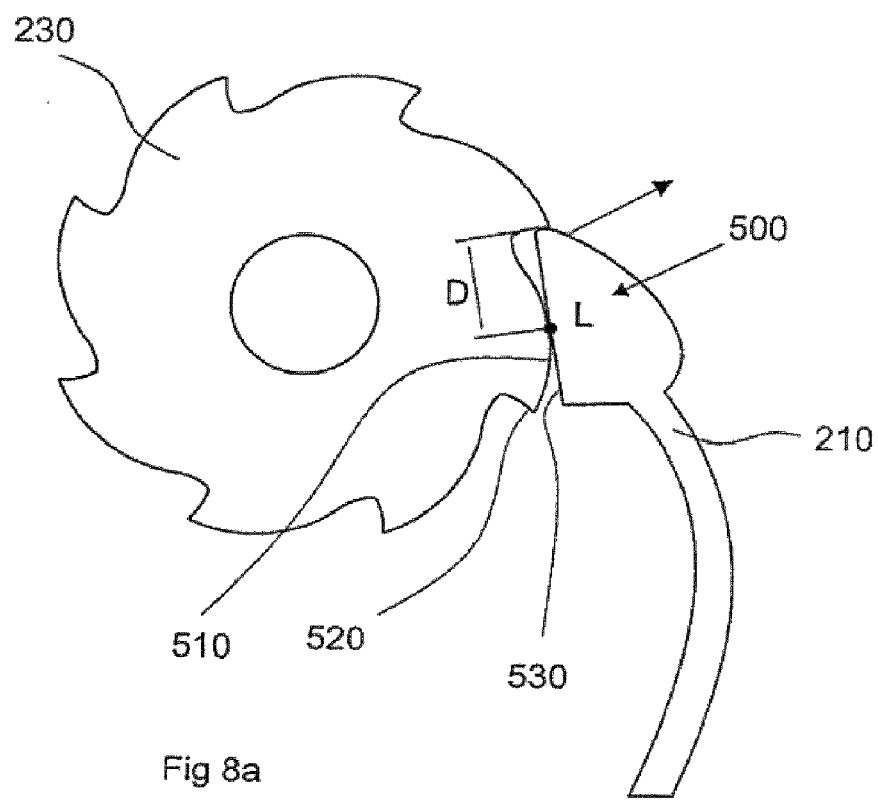
FIGS. 8a and 8b shows the basic geometry of two possible pawl and ratchet arrangement provided with lever means in accordance with the present invention.
Figure 8B:
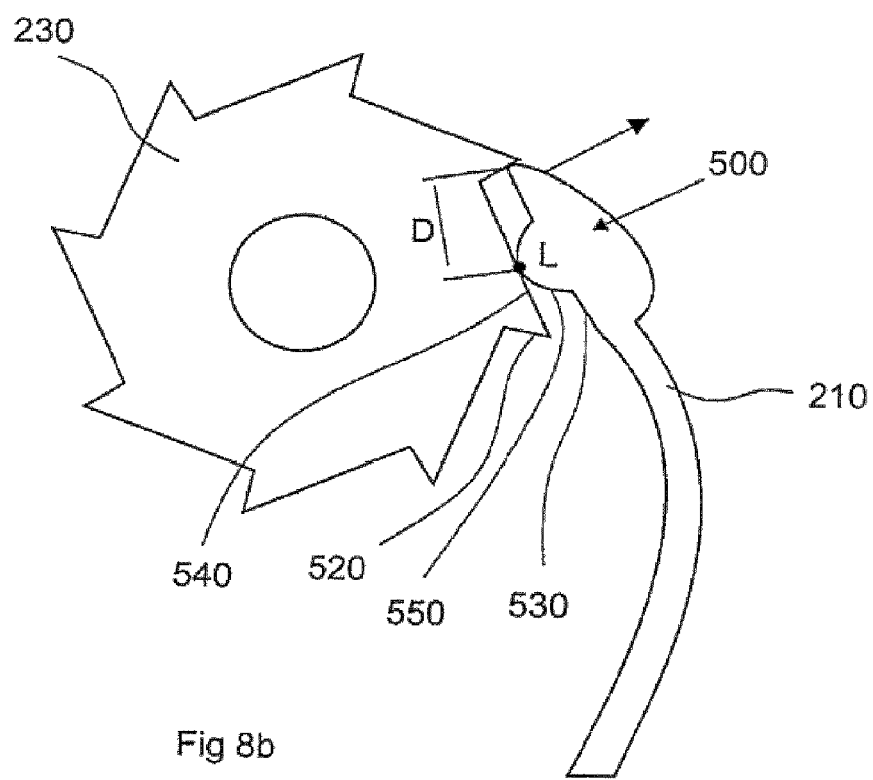

In order to overcome the tendency of the pawl 210 to flex radially inwardly towards the axis of rotation of the ratchet wheel at the point of disengagement, the point of disengagement is effectively controlled in that the pawl and ratchet arrangement is provided with lever means arranged to effect the disengagement of the pawl from a tooth on the ratchet wheel. The lever means are designed so as to establish abutment of the pawl and the ratchet wheel at a lever point following said tooth with respect to the direction of the rotational motion. FIGS. 8a and 8b show examples of two possible embodiments of lever means 500 to control disengagement of the pawl 210 from the ratchet wheel 230. In order for the lever means 500 to function as disengagement controlling means, it has to be designed so that the lever point L is located a suitable distance D from the tip of the pawl head, depending on desired disengagement angle, and design and material characteristics of the pawl 210 and the ratchet wheel 230. In the embodiment of FIG. 8a, the lever means 500 is formed by a convex back surface 510 of the ratchet wheel teeth 520 and a low profile pawl counter surface 530. In the embodiment of FIG. 8b, the lever means 500 is formed by a flat back surface 540 of the ratchet wheel teeth 520 and a protrusion 550 on the pawl counter surface 530.

Figure 9A:
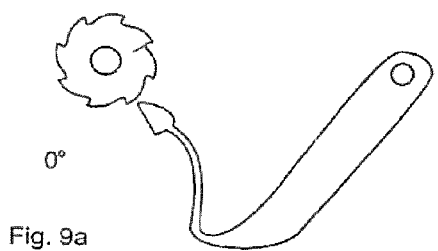
FIGS. 9a to 9h show engagement and disengagement of the pawl and ratchet arrangement.
Figure 9B:
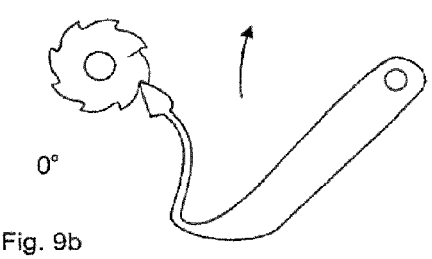
Figure 9C:
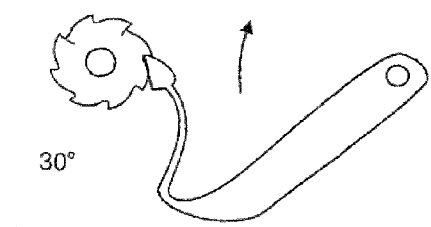
Figure 9D:
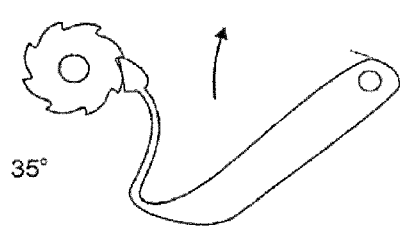
Figure 9E:
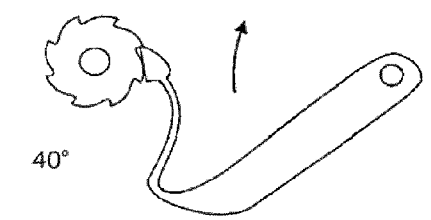
Figure 9F:
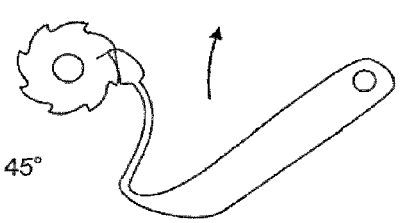
Figure 9G:
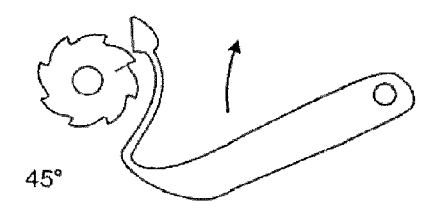
Figure 9H:
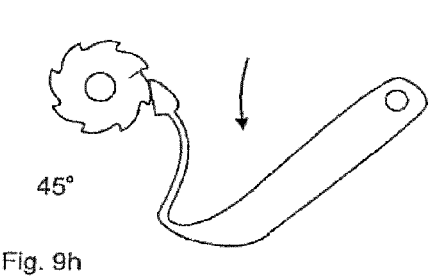

FIGS. 9a to 9h show the engagement and disengagement sequence for the ratchet wheel and pawl mechanism 190 according to one embodiment of the present invention. From this sequence it can be seen in FIG. 9d, that the pawl and the teeth on the ratchet wheel are formed so that a lever point of abutment is established at an angle preceding the desired disengagement angle. Thereafter in FIG. 9e it can be seen that the lever action forces the tip of the pawl head in the disengagement direction with respect to the tip of the tooth on the ratchet wheel. When the desired disengagement angle is reached, as is shown in FIGS. 9f and 9g, the lever action eventually effects the controlled disengagement of the pawl head from the tooth on the ratchet wheel. FIG. 9h illustrates the reset motion of the rocker arm, whereby the ratchet wheel is prevented from back rotation by the friction brake 280, as will be discussed in more detail below.

As is shown in FIGS. 8a-9h the lever point on the ratchet wheel can be located on the back surface of the subsequent tooth, but it could be located at any suitable point on the ratchet wheel.

Compared to the use of a separate control surface according to U.S. Pat. No. 6,446,627, the provision of lever means 500 to control the disengagement, has the clear advantage that it is based solely on the direct interaction between the pawl 210 and the ratchet wheel 230 and does not depend on additional parts. As mentioned above, dose counters for inhaler devices are restrained to small size and low cost, at the same time as the accuracy must be high. Therefore any reduction of the number of interacting parts increases the accuracy.

Figure 10:
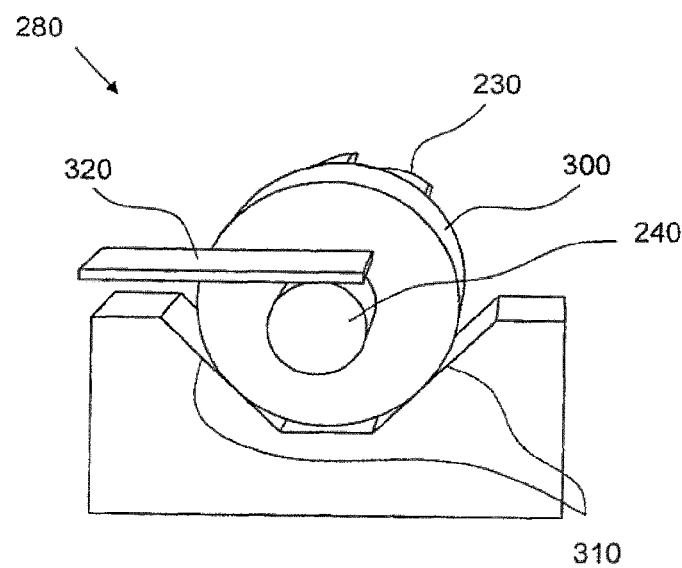
FIG. 10 is a cut out perspective view of a back rotation brake arrangement in the counter mechanism of FIGS. 4a to 4c.

FIG. 10 is a cut out perspective view of a back rotation brake arrangement 280 in the counter mechanism 190 of FIGS. 4a to 4c. The present embodiment of the back rotation prevention brake 280 is comprised of a cylindrical element 300 supported by two inclined friction surfaces 310 in V-arrangement, the cylindrical element 300 being coupled to the rotational movement of the ratchet wheel 230 and pawl mechanism and urged against the friction surfaces 310 by a spring member 320. In the disclosed embodiment, the inclined friction surfaces are parallel to the axis of rotation for the cylindrical element 300.

Figure 11A:
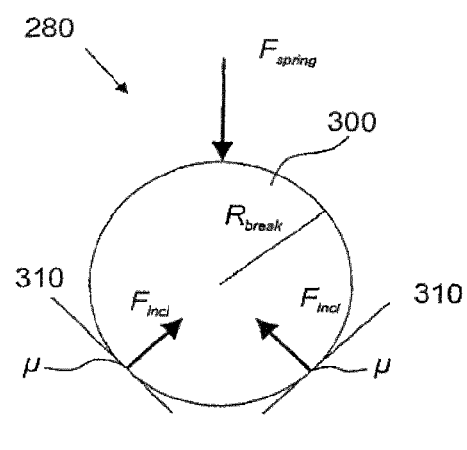
FIGS. 11a and 11b schematically show the forces present in the back rotation brake of FIG. 9.
Figure 11B:
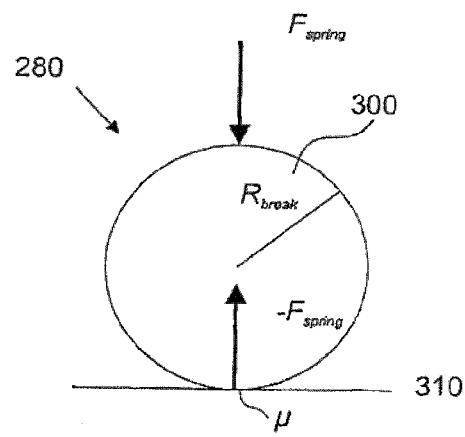

FIG. 11a schematically shows the forces present in the back rotation brake 280 of FIG. 9, whereas FIG. 11b shows the forces present in a single friction surface 310 friction brake. The frictional torque $M_{brake}$ braking rotation of the cylindrical element 300 in the latter case (11b) is simply (assuming that the friction torque between the spring member 320 and the axle 240 is negligible):

$$M_{brake} = F_{spring} \mu R_{brake}$$

where $F_{spring}$ is the vertical force from the spring 320, $\mu$ is the sliding frictional coefficient between the cylindrical element 300 and the friction surface 310, and $R_{brake}$ is the radius of the cylindrical element 300.

In the former case (11a) the normal forces $F_{incl}$ acting on the cylindrical element 300 by the inclined surfaces 310 gives the following frictional torque $M_{brake}$:

$$M_{break} = 2F_{incl} \mu R_{break}$$

In the embodiment of FIG. 11a, the inclined surfaces 310 are inclined +–45° respectively, with respect to the direction of $F_{spring}$, whereby the resulting frictional torque $M_{brake}$ becomes:

$$M_{break} = \sqrt{2} F_{spring} \mu R_{break}$$

Thus the resulting frictional torque is a factor $\sqrt{2}=1,41$ higher than in the case of one single flat friction surface 310. By selecting the inclination angles for the inclined surfaces 310, the spring force $F_{spring}$ and the frictional coefficient between the cylindrical element 300 and the inclined surfaces 310, the brake torque can be controlled to a predefined value as required by the counter mechanism design. In the present embodiment, the angle between the friction surfaces is less than 120°, preferably less than 110°, and more preferably less than 100°, and greater than 60°, preferably greater than 75°, and more preferably greater than 80°. Even though it theoretically would be even more efficient with an greater number of friction surfaces 310 or points of frictional contact, the number is preferably limited to two surfaces 310 as it, in a mass production situation, is more difficult to control the individual resulting force components for more than two surfaces 310.

In the present embodiment (FIGS. 4a to 11a) the spring member 320 applies a force $F_{spring}$ on the cylindrical element 300 in a direction essentially opposite the direction of movement of the pawl 210 when advancing the display means by incremental rotation of the ratchet wheel 230 and the axle assembly 240. By this arrangement, the force applied by the pawl 210 on the ratchet wheel 230, will result in a lowered brake torque $M_{brake}$ and the rotation of the ratchet wheel 230 in the forward direction will be easier. However, during its reset motion, the pawl 210 will apply a force essentially in alignment with the spring force $F_{spring}$, whereby the brake torque $M_{brake}$ will increase and rotation in the backwards direction effectively will be prevented.

In order to assure that the desired brake torque $M_{brake}$ is achieved, the back rotation prevention means 280 functions as bearing for one end of the axle arrangement 240. According to the disclosed embodiment of FIGS. 5a to 6b, the axle arrangement is provided with second bearing means 430 at the worm gear 290 end, and lateral positioning means 440 in between the back rotation means 280 and the worm gear 290.

Figure 12:
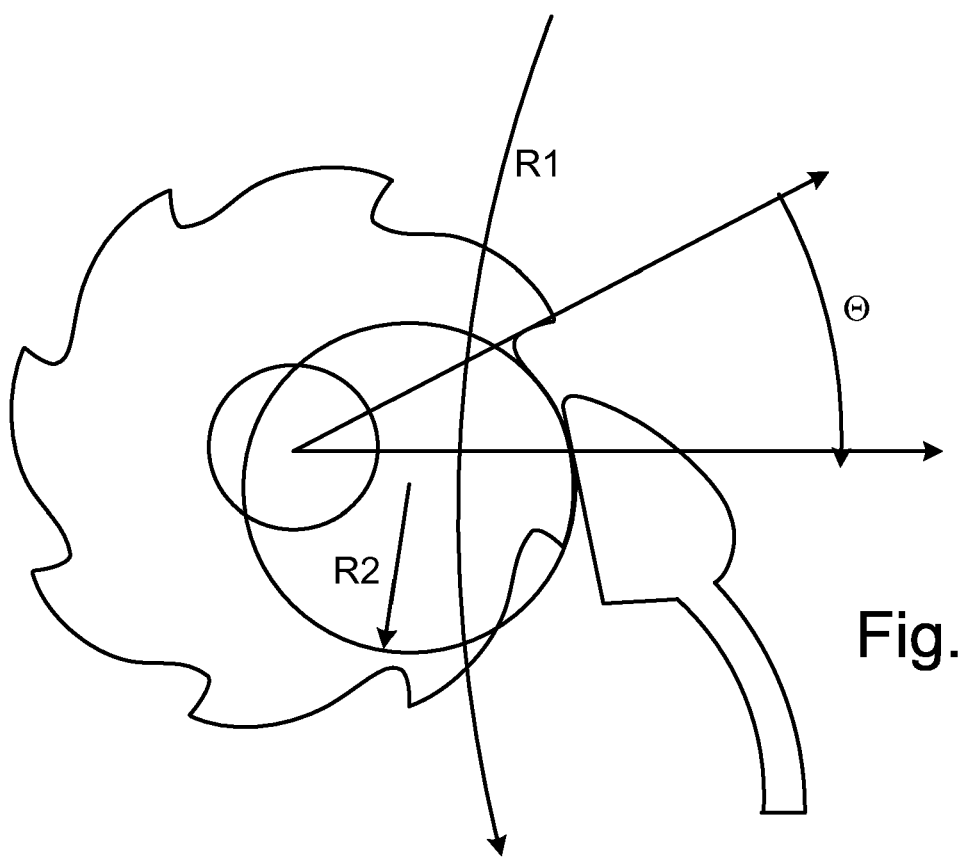
FIG. 12 shows the basic geometry of the ratchet wheel in the counter mechanism of FIGS. 4a to 4c.
Figure 13:
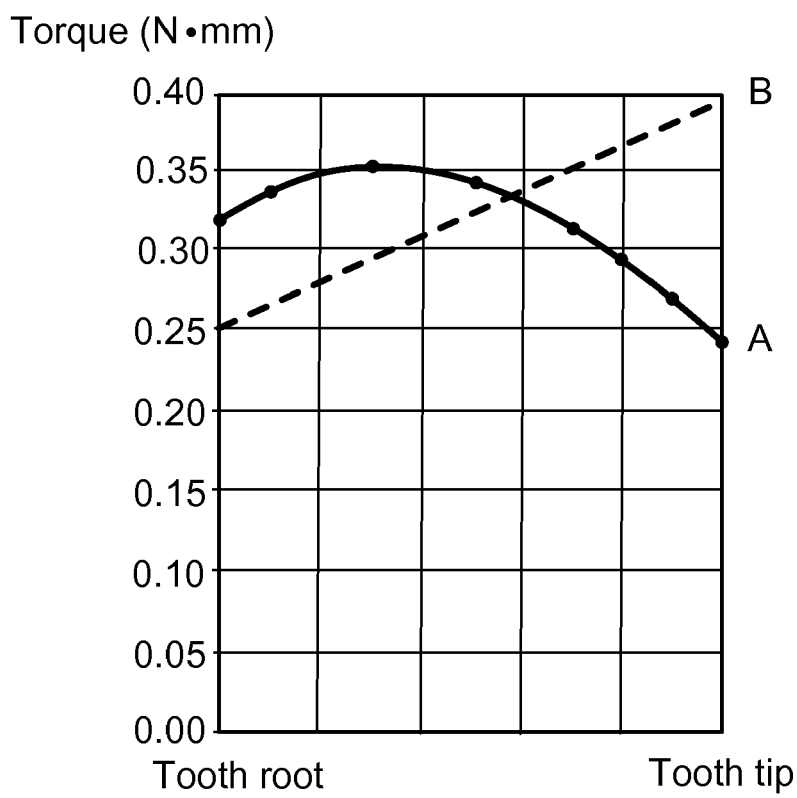
FIG. 13 is a graph showing the reset torque applied by a pawl on the ratchet wheel of FIG. 12.

In order to further reduce the risk of back rotation of the ratchet wheel 230 during the reset motion of the pawl 210, the geometry of the ratchet teeth has been optimised to minimise the maximum reset torque applied by the pawl 210 on the ratchet wheel 230. The optimum geometry derived from this optimization is teeth with a convex back surface as is shown in FIG. 12. FIG. 13 shows the resulting reset torque vs. reset angle for a convex tooth back as a solid line A, and for a conventional flat toothback (see FIG. 8b) as a dotted line B. Compared with a tooth with a flat back surface, the tooth with a convex back surface has a higher initial torque as the pawl tip is forced towards its center of rotation early on during the reset motion, but thereafter the torque drops as the tip of the pawl approaches the tooth tip. The higher torque at the start coincides with the spring being compressed; therefore the spring is able to provide the necessary reset torque. Whereas the reset torque for the tooth with a flat back surface is a linear increase and reaches its maximum torque at the tooth tip, the maximum torque being higher for the flat backed tooth and also the peak coincides with the spring being extended, therefore it is less able to provide the required reset torque.

The curvature of the convex back surface is selected to minimise the maximum reset torque for the ratchet wheel and pawl mechanism by calculations of the reset torque from the parameters comprising: ratchet wheel diameter, ratchet teeth back surface curvature, friction coefficient between the ratchet wheel material and the pawl material, and pawl spring constant.

There is also provided a method of providing a ratchet wheel and pawl mechanism for transforming a linear actuation motion into a rotational motion advancing a display means indicating the number of doses available in an inhaler comprising the steps:

selecting diameter, number of teeth and material for the ratchet wheel, selecting shape and material for the pawl, minimizing the maximum reset torque for the ratchet wheel and pawl mechanism by providing the ratchet wheel teeth with a convex back surface, wherein the step of providing the ratchet wheel teeth with a convex back surface comprises finding the ratchet teeth back surface curvature by calculations of the reset torque from the parameters comprising: ratchet wheel diameter, friction coefficient between the ratchet wheel material and the pawl material, and pawl spring constant.

The invention claimed is:

1. An inhaler counter comprising a ratchet wheel, a pawl and a display, the ratchet wheel and the pawl being arranged to transform a linear actuation motion into a rotational motion that advances the display by the pawl engaging a tooth of the ratchet wheel, the pawl and ratchet wheel arranged to effect disengagement of the pawl from the engaged tooth of the ratchet wheel by establishing abutment of the pawl and ratchet wheel at a lever point following the engaged tooth with respect to a direction of rotational motion of the ratchet wheel;

wherein the lever point on the ratchet wheel is located on a tooth subsequent to the engaged tooth; and, wherein the subsequent tooth includes a straight back surface and the pawl includes a protrusion on a pawl counter surface that abuts the straight back surface to form the lever point.

2. An inhaler comprising:

an inhaler canister;

an actuator body receiving the inhaler canister, the inhaler being actuated by linear motion of the canister relative to the actuator body; and an inhaler counter according to claim 1 coupled to the inhaler canister.

3. An inhaler counter comprising:

a ratchet wheel and a pawl, the ratchet wheel and the pawl being arranged to transform a linear actuation motion into a rotational motion advancing a display by the pawl engaging a tooth of the ratchet wheel, wherein the ratchet wheel has teeth with a convex back surface, the ratchet wheel and the pawl having a maximum reset torque dependent on a curvature of the convex back surface, a diameter of the ratchet wheel, a friction coefficient between the ratchet wheel material and the pawl material, and a spring constant of the pawl, wherein the curvature of the convex back surface is selected to minimize the maximum reset torque.

4. An inhaler comprising:

an inhaler canister;

an actuator body receiving the inhaler canister, the inhaler being actuated by linear motion of the canister relative to the actuator body; and an inhaler counter according to claim 3 coupled to the inhaler canister.

5. A method of providing a ratchet wheel and a pawl arranged to transform a linear actuation motion into a rotational motion advancing a display by the pawl engaging a tooth of the ratchet wheel, the method comprising:

selecting diameter, number of teeth, and material for the ratchet wheel, the teeth having a convex back surface;

selecting shape and material for the pawl;

determining a maximum reset torque for the ratchet wheel and pawl arrangement as a function of ratchet wheel diameter, friction coefficient between the ratchet wheel material and the pawl material, pawl spring constant, and curvature of the convex back surface; and selecting the curvature of the convex back surface so as to minimize the maximum reset torque.

* * * * *